(12) United States Patent
Paulk et al.

(10) Patent No.: US 8,974,494 B2
(45) Date of Patent: Mar. 10, 2015

(54) SURGICAL DEVICES

(75) Inventors: David A. Paulk, Hopedale, MA (US); Paul L. Salvas, Norton, MA (US); Richard Lunn, Kingston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1101 days.

(21) Appl. No.: 12/503,180

(22) Filed: Jul. 15, 2009

(65) Prior Publication Data
US 2010/0016869 A1 Jan. 21, 2010

Related U.S. Application Data

(60) Provisional application No. 61/081,462, filed on Jul. 17, 2008.

(51) Int. Cl.
*A61B 17/04* (2006.01)

(52) U.S. Cl.
CPC ..... *A61B 17/0401* (2013.01); *A61B 2017/0409* (2013.01); *A61B 2017/0451* (2013.01)
USPC ............................ 606/232; 606/104; 606/144

(58) Field of Classification Search
USPC ......... 606/60, 86 A, 104, 139, 144, 124, 228, 606/232, 300–321, 916, 103, 142; 81/436
See application file for complete search history.

(56) References Cited

U.S. PATENT DOCUMENTS

| | | | |
|---|---|---|---|
| 5,258,016 A * | 11/1993 | DiPoto et al. | 606/232 |
| 5,356,435 A | 10/1994 | Thein | |
| 5,376,119 A | 12/1994 | Zimmermann et al. | |
| 5,584,835 A | 12/1996 | Greenfield | |
| 5,584,860 A * | 12/1996 | Goble et al. | 606/232 |
| 5,607,432 A * | 3/1997 | Fucci | 606/104 |
| 5,827,291 A * | 10/1998 | Fucci et al. | 606/104 |
| 5,849,004 A * | 12/1998 | Bramlet | 606/232 |
| 5,948,000 A * | 9/1999 | Larsen et al. | 606/232 |
| 6,152,934 A * | 11/2000 | Harper et al. | 606/139 |
| 6,159,235 A | 12/2000 | Kim | |
| 6,206,886 B1 | 3/2001 | Bennett | |

(Continued)

FOREIGN PATENT DOCUMENTS

| | | |
|---|---|---|
| EP | 1884198 A3 | 4/2008 |
| WO | 2005037055 | 4/2005 |
| WO | 2008054814 | 5/2008 |

OTHER PUBLICATIONS

International Search Report and Written Opinion for PCT/US2009/050620 Dated Sep. 29, 2009.

(Continued)

*Primary Examiner* — Ashley Fishback
*Assistant Examiner* — Jing Ou
(74) *Attorney, Agent, or Firm* — Norman F. Hainer, Jr.

(57) ABSTRACT

The present disclosure relates to a surgical device including a shaft having an outer member and an inner member slidably received within the outer member, a handle coupled to the shaft, and a combination of a cannulated body having a distal end and a proximal end, a plug including a top portion configured for engagement with the proximal end of the body and a bottom portion coupled to the top portion, a first portion disposed on the bottom portion of the plug, a second portion disposed on the bottom portion of the plug, and a spring located between the first and second portions for providing movement to the inner member coupled to the inner member. A method of tissue repair is also disclosed.

2 Claims, 12 Drawing Sheets

(56) References Cited

U.S. PATENT DOCUMENTS

| | | | |
|---|---|---|---|
| 6,228,096 B1* | 5/2001 | Marchand | 606/139 |
| 6,436,142 B1* | 8/2002 | Paes et al. | 623/17.15 |
| 6,517,542 B1* | 2/2003 | Papay et al. | 606/232 |
| 6,575,987 B2 | 6/2003 | Gellman et al. | |
| 6,692,516 B2 | 2/2004 | West et al. | |
| 7,083,638 B2 | 8/2006 | Foerster | |
| 7,517,357 B2 | 4/2009 | Abrams et al. | |
| 7,585,311 B2 | 9/2009 | Green et al. | |
| 7,604,640 B2* | 10/2009 | Kana | 606/99 |
| 7,938,847 B2 | 5/2011 | Fanton et al. | |
| 8,118,835 B2 | 2/2012 | Weisel et al. | |
| 8,133,258 B2 | 3/2012 | Foerster et al. | |
| 8,137,381 B2 | 3/2012 | Foerster et al. | |
| 8,162,978 B2 | 4/2012 | Lombardo et al. | |
| 2002/0161401 A1* | 10/2002 | Steiner | 606/232 |
| 2002/0188301 A1* | 12/2002 | Dallara et al. | 606/104 |
| 2003/0083669 A1* | 5/2003 | Gleason | 606/103 |
| 2003/0088272 A1* | 5/2003 | Smith | 606/232 |
| 2003/0187446 A1* | 10/2003 | Overaker et al. | 606/73 |
| 2003/0208210 A1 | 11/2003 | Dreyfuss et al. | |
| 2004/0098050 A1 | 5/2004 | Foerster et al. | |
| 2004/0133239 A1* | 7/2004 | Singhatat | 606/232 |
| 2004/0225313 A1* | 11/2004 | Kanner et al. | 606/184 |
| 2005/0033364 A1 | 2/2005 | Gregoire et al. | |
| 2005/0055052 A1* | 3/2005 | Lombardo et al. | 606/232 |
| 2005/0216015 A1* | 9/2005 | Kreidler | 606/73 |
| 2005/0245932 A1 | 11/2005 | Fanton et al. | |
| 2006/0004364 A1 | 1/2006 | Green et al. | |
| 2006/0271060 A1 | 11/2006 | Gordon | |
| 2007/0203498 A1 | 8/2007 | Gerber | |
| 2007/0225736 A1 | 9/2007 | Zeiner et al. | |
| 2008/0009904 A1* | 1/2008 | Bourque et al. | 606/232 |
| 2008/0015594 A1 | 1/2008 | Ritchart et al. | |
| 2008/0033460 A1 | 2/2008 | Ziniti et al. | |
| 2008/0051836 A1* | 2/2008 | Foerster et al. | 606/232 |
| 2008/0215061 A1* | 9/2008 | Schumacher et al. | 606/104 |
| 2008/0281353 A1* | 11/2008 | Aranyi et al. | 606/219 |
| 2009/0112270 A1 | 4/2009 | Lunn et al. | |

OTHER PUBLICATIONS

First Office Action regarding Japanese Patent Application No. 200980127858.1 mailed Aug. 22, 2012.

Office Action received for corresponding Japanese application No. 2011-518863 mailed Mar. 31, 2014.

Office Action received in corresponding Japanese patent application No. 2011-518863 mailed Sep. 10, 2013.

Office action received in corresponding Australian patent application No. 2009270960 mailed May 9, 2014.

* cited by examiner

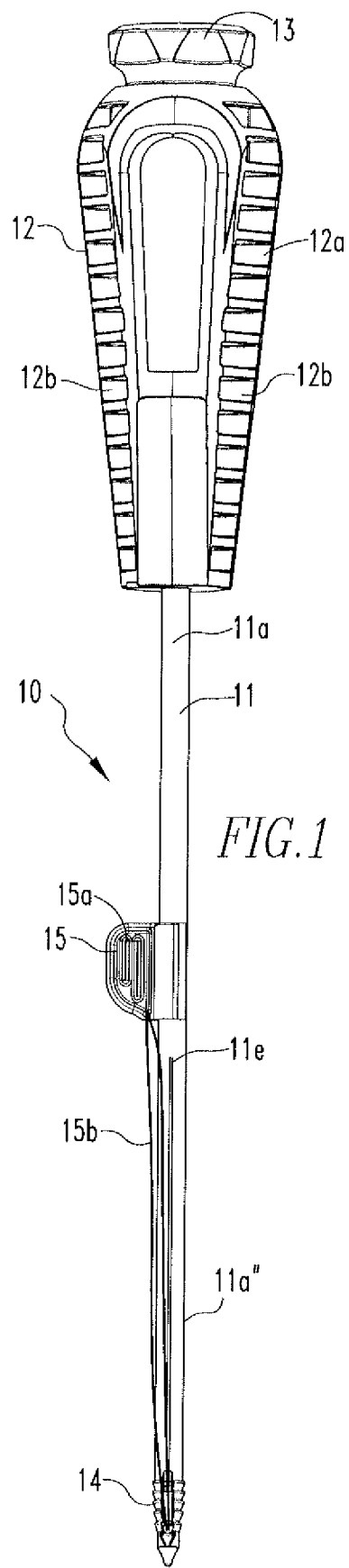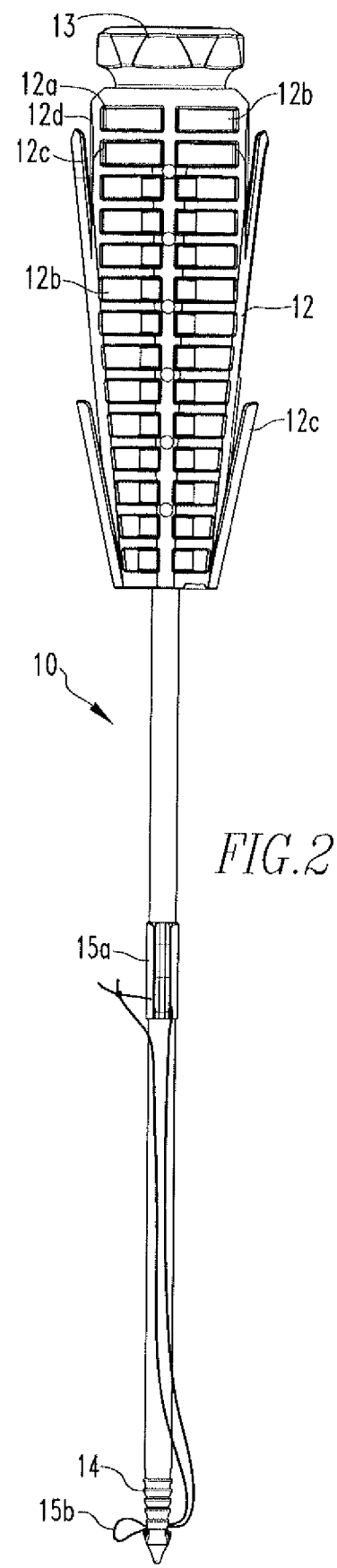

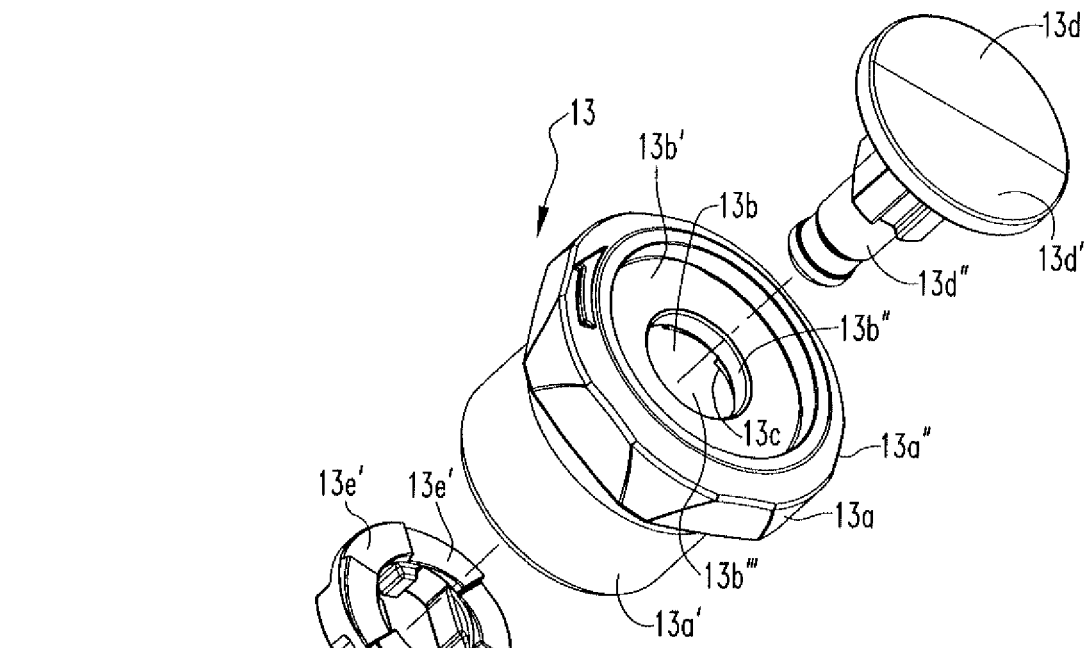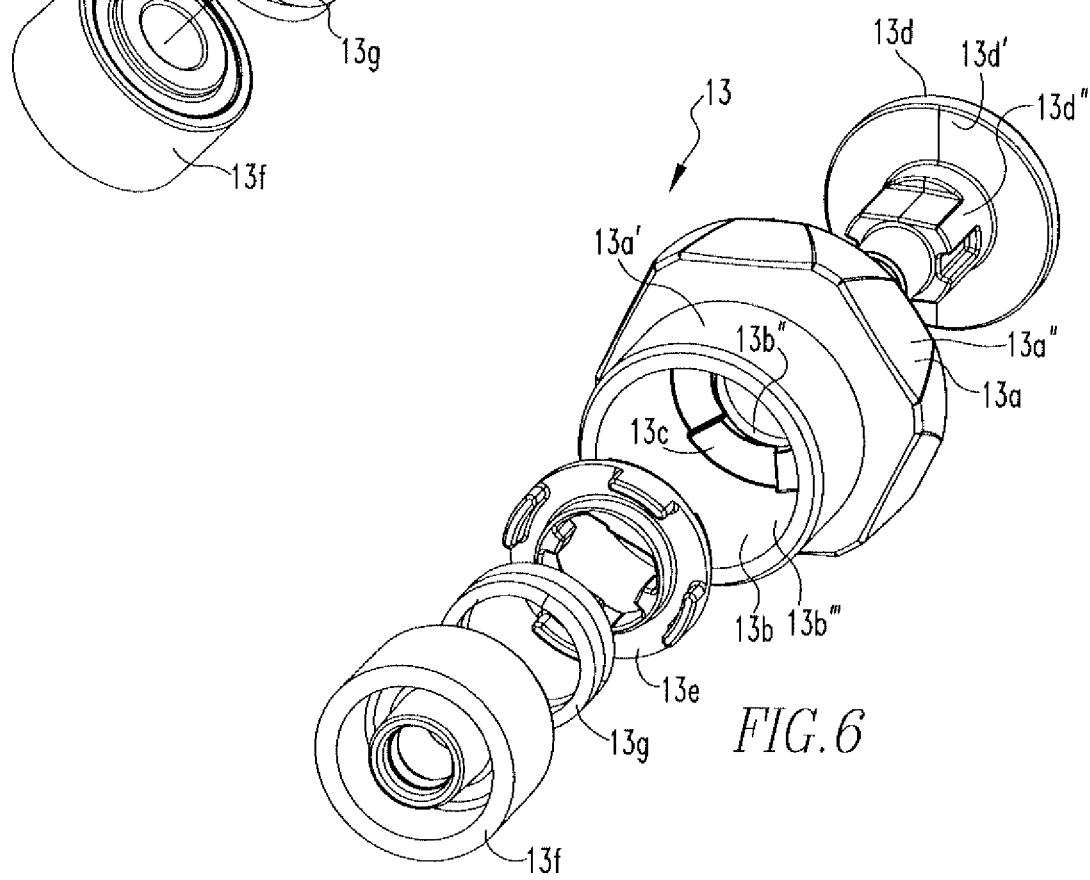

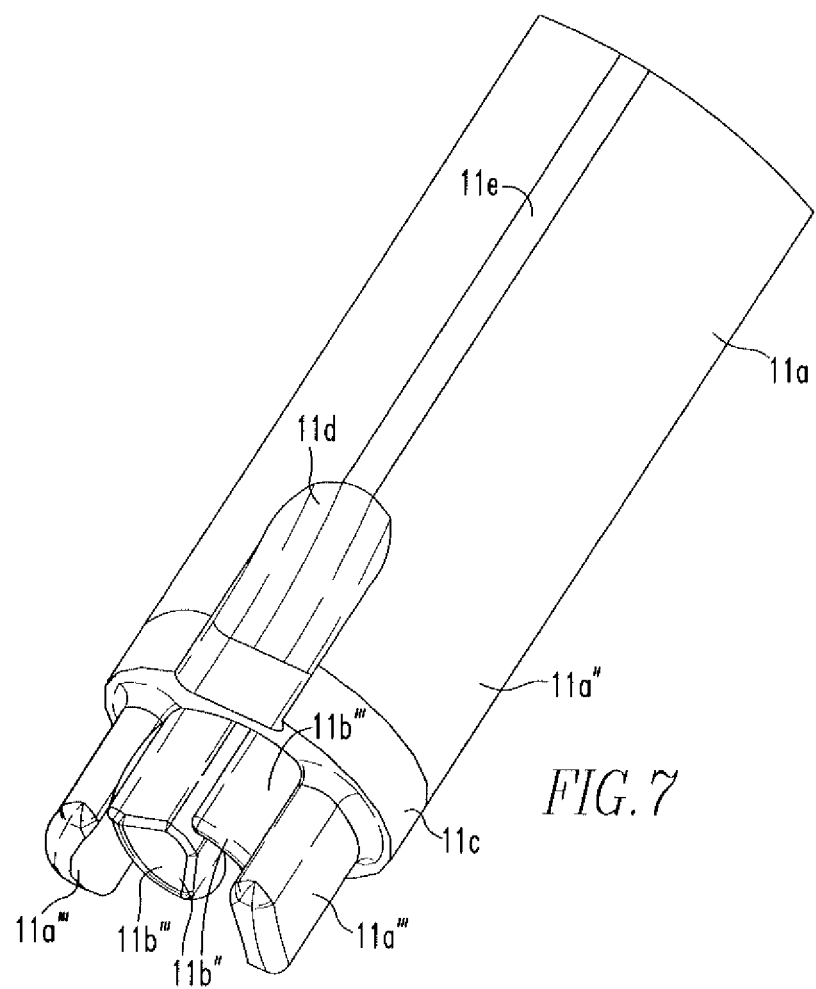

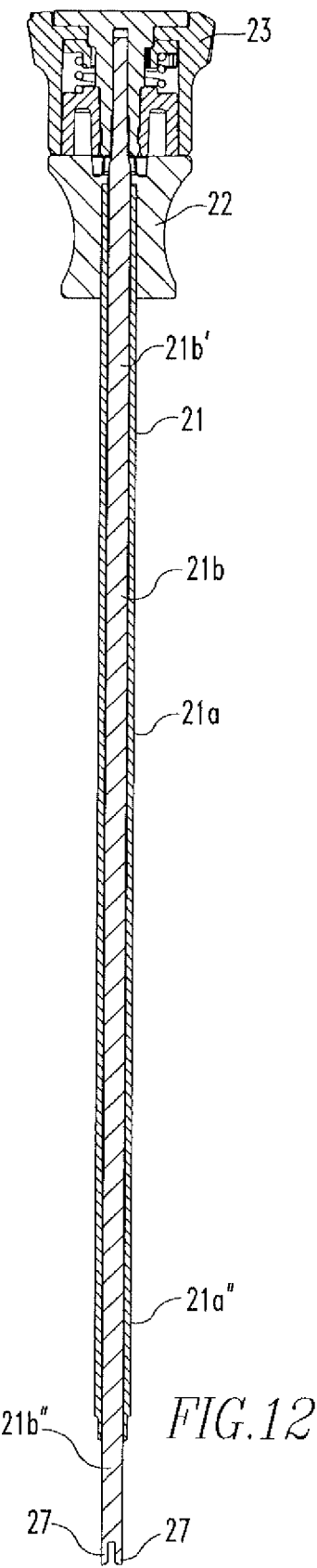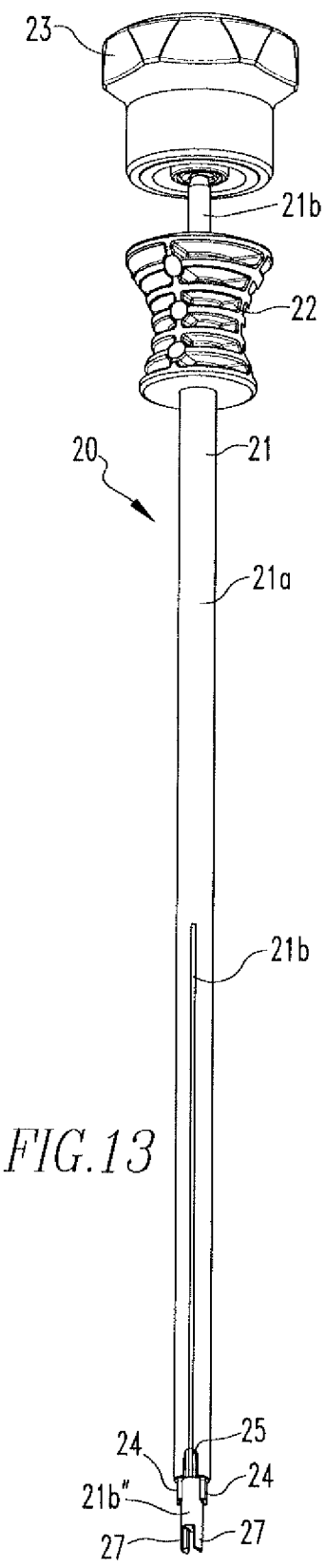

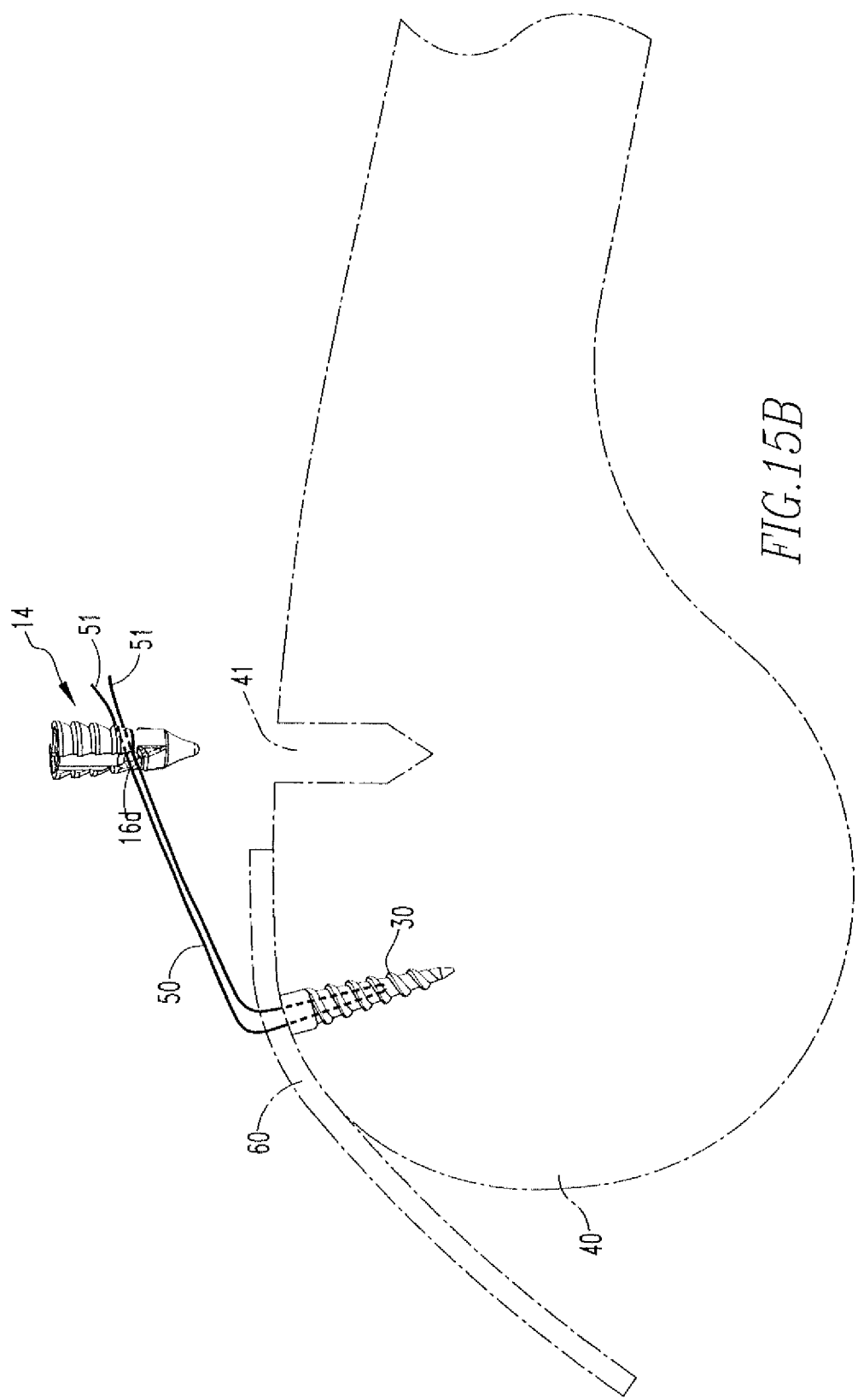

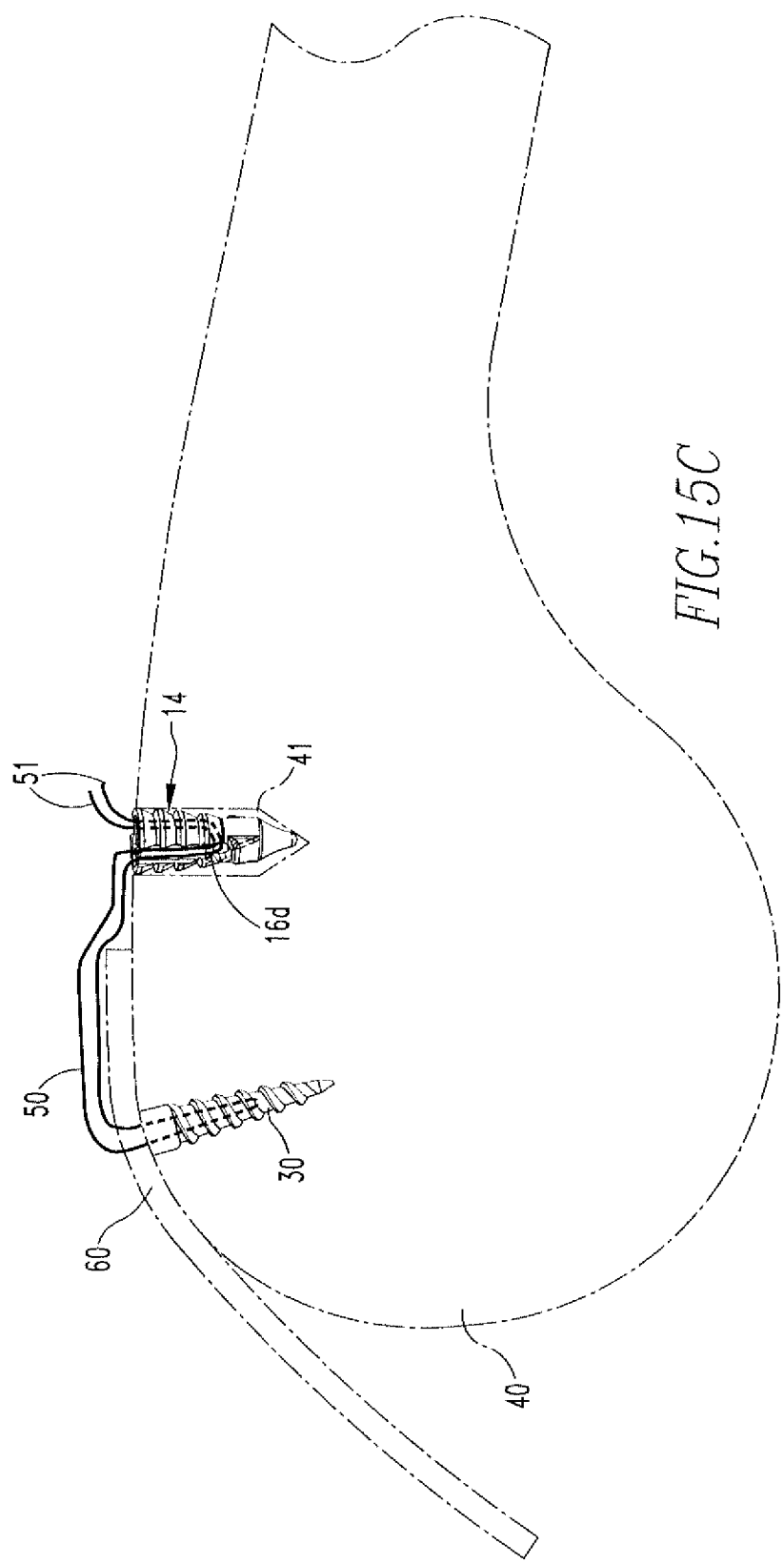

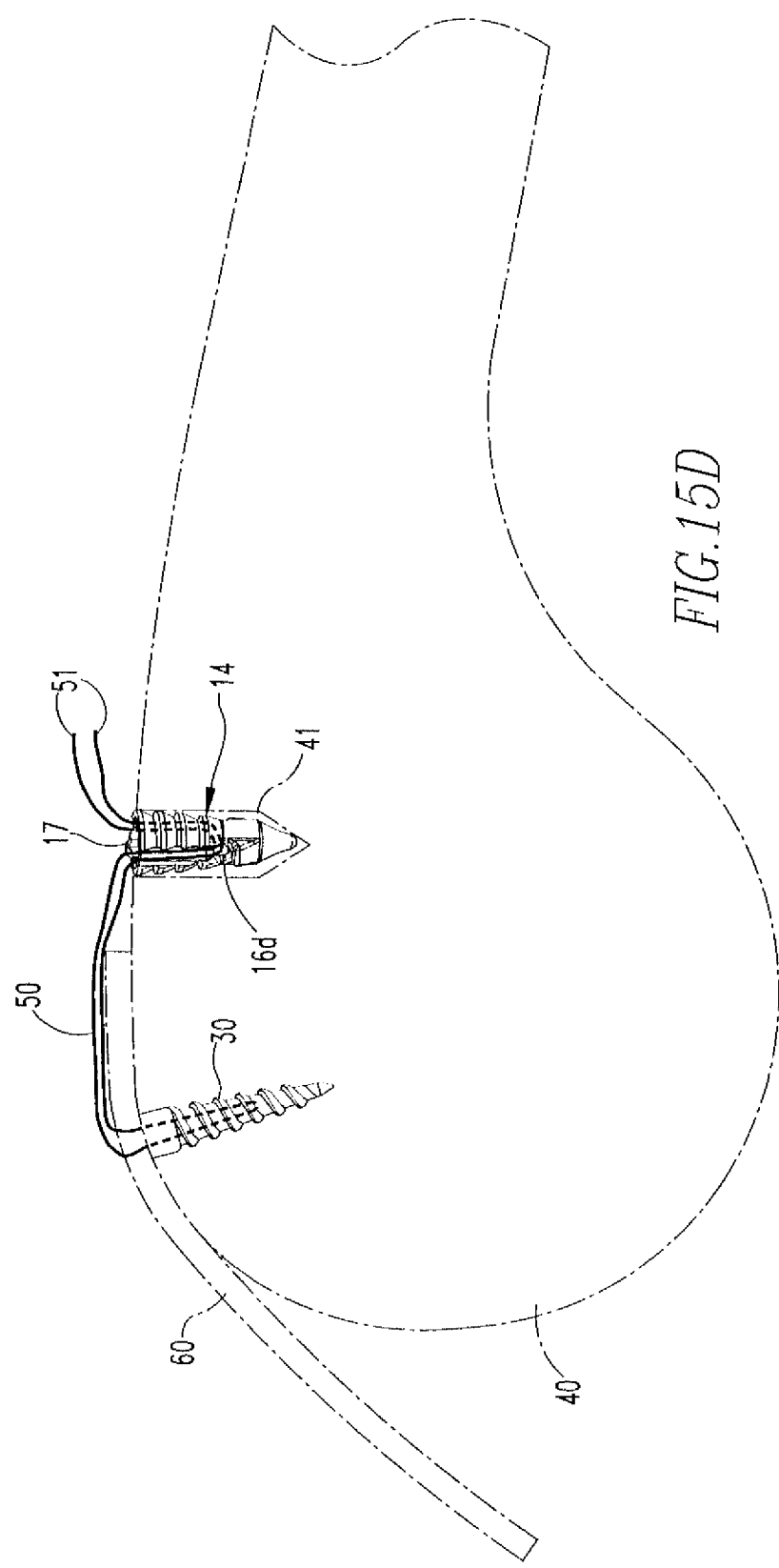

SURGICAL DEVICES

CROSS REFERENCE TO RELATED APPLICATIONS

This application claims priority to U.S. Patent Application No. 61/081,462 filed on Jul. 17, 2008, the disclosure of which is incorporated herein by reference in its entirety.

BACKGROUND

1. Technical Field

The present disclosure relates to surgical devices for use in tissue repair.

2. Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and devices for use in such procedure, that securely attaches tissue to bone using a plurality of attachment points over a large area of contact is needed.

SUMMARY

The present disclosure relates to a surgical device including; a shaft having an outer member and an inner member slidably received within the outer member, a handle coupled to the shaft, and a means for providing movement to the inner member coupled to the inner member. In an embodiment, the surgical device further comprises an anchor assembly coupled to the device, wherein the anchor assembly comprises an anchor defining a cavity and an insertion member housed within the cavity. In another embodiment, the outer member includes a distal portion configured to engage the anchor and the inner member includes a distal portion configured to engage the insertion member. In yet another embodiment, the surgical device further comprises a suture threader coupled to the shaft, wherein the threader includes a clip and a loop of suture coupled to the clip. In a further embodiment, the loop of suture is disposed within a transverse through hole extending through the anchor.

In a further embodiment, the means for providing movement to the inner member includes a cannulated body having a distal end and a proximal end, a plug including a top portion configured for engagement with the proximal end of the body and a bottom portion coupled to the top portion, a first portion disposed on the bottom portion of the plug, a second portion disposed on the bottom portion of the plug, and a spring located between the first and second portions. In yet a further embodiment, the proximal end of the body includes gears. In an embodiment, the first portion includes gears configured for engagement with the gears of the proximal end of the body. In another embodiment, the outer member is shorter than the inner member.

In another aspect, the present disclosure relates to a method of tissue repair including inserting a first anchor into bone, the first anchor having a flexible member coupled thereto; passing ends of the flexible member through the tissue; providing a surgical device including a shaft having an outer member and an inner member slidably received within the outer member, a handle coupled to the shaft, a means for providing movement to the inner member coupled to the inner member, and an anchor assembly coupled to the shaft, the anchor assembly comprising an anchor defining a cavity and a transverse through hole and an insertion member housed within the cavity; passing at least one end of the flexible member through the through hole of the anchor assembly; placing the anchor assembly into bone; advancing the insertion member toward the at least one end of the flexible member to secure the flexible member in the through hole and the tissue to bone.

In an embodiment, the method further includes tensioning the flexible member before advancement of the insertion member. In another embodiment, advancement of the insertion member includes rotation of the means for providing movement to the inner member. The means includes a cannulated body having a distal end and a proximal end, a plug including a top portion configured for engagement with the proximal end of the body and a bottom portion coupled to the top portion, a first portion disposed on the bottom portion of the plug, a second portion disposed on the bottom portion of the plug, and a spring located between the first and second portions. In yet another embodiment, the proximal end of the body includes gears. In a further embodiment, the first portion includes gears configured for engagement with the gears of the proximal end of the body, wherein the means is rotated to advance the insertion member until the gears of the first portion and the gears of the proximal end are no longer in direct engagement.

In an embodiment, the method further includes providing a surgical device having a shaft including an outer member and an inner member slidably received within the outer member, a handle coupled to the shaft, and a means for providing movement to the inner member coupled to the inner member, wherein the outer member is shorter than the inner member; placing the surgical device into engagement with the anchor assembly such that the inner member is engaged with the insertion member and the outer member is engaged with the anchor; moving the insertion member away from the at least one end of the flexible member; tensioning the flexible member; and advancing the insertion member back toward the flexible member to re-secure the flexible member.

In yet another embodiment, advancement of the insertion member toward the flexible member includes rotation of the means for providing movement to the inner member. The means includes a cannulated body having a distal end and a proximal end, a plug including a top portion configured for engagement with the proximal end of the body and a bottom portion coupled to the top portion, a first portion disposed on the bottom portion of the plug, a second portion disposed on the bottom portion of the plug, and a spring located between the first and second portions. In a further embodiment, the proximal end of the body includes gears. In yet a further embodiment, the first portion includes gears configured for engagement with the gears of the proximal end of the body, wherein the means is rotated to advance the insertion member until the gears of the first portion and the gears of the proximal end are no longer in direct engagement.

Further areas of applicability or the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 1 shows a perspective view of a first surgical device of the present disclosure.

FIG. 2 shows another perspective view of the surgical device of FIG. 1.

FIG. 5 shows an exploded view of the means for providing movement of the inner member of FIG. 4.

FIG. 6 shows another exploded view of the means for providing movement of the inner member of FIG. 4.

FIG. 7 shows a perspective view of the distal portions of the inner and outer members of the surgical device of FIG. 1.

FIG. 12 shows a cross-sectional view of the second surgical device of FIG. 11.

FIG. 13 shows another perspective view of the second surgical device of FIG. 11.

FIGS. 15A-15D show use of the first surgical device of the present disclosure in repairing tissue.

DETAILED DESCRIPTION OF THE EMBODIMENTS

The following description of the preferred embodiment(s) is merely exemplary in nature and is in no way intended to limit the disclosure, its application, or uses.

Figure 3:
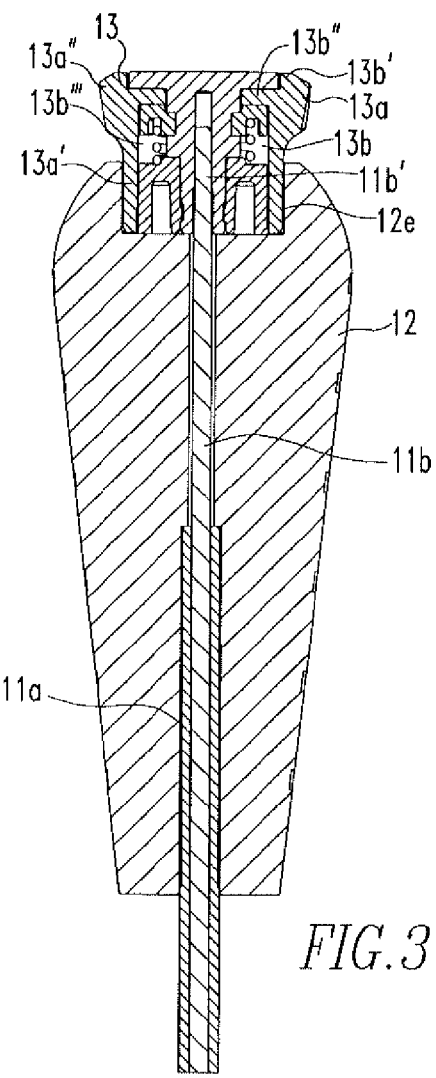
FIG. 3 shows a cross-sectional view of the handle of the surgical device of FIG. 1.
Figure 4:
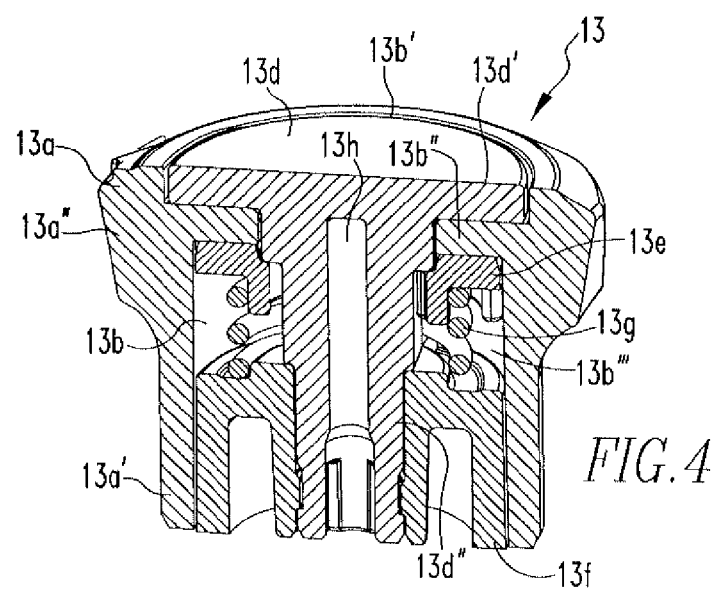
FIG. 4 shows a cross-sectional view of the means for providing movement of the inner member of the surgical device of FIG. 1.

FIGS. 1-3 show perspective views of the first surgical device 10 of the present disclosure. The device 10 includes a shaft 11 having an outer member 11a and an inner member 11b slidably received within the outer member 11a. Coupled to the shaft 11 is a handle 12 having a body 12a with grooves 12b extending through the body 12a and projections 12c located on the outer surface 12d of the body 12a. A means 13 for providing movement to the inner member, as more clearly shown in FIGS. 4-6 and as more fully explained below, is housed within an opening 12e on the handle 12 and is coupled to a proximal portion 11b' of the inner member 11b.

Also coupled to the shaft 11, specifically the distal portions 11a",11b" (FIG. 7) of the outer and inner members 11a,11b, is an anchor assembly 14, as more clearly shown in FIGS. 8-10 and as more fully described below. The distal portion 11a" of the outer member 11a includes a first laser mark 11c, for purposes to be described later, and at least two divets 11d for housing of suture, as will be more fully described below. A second laser mark 11e extends a partial length of the outer member 11a. At least two prongs 11a''' extend longitudinally from the distal portion 11a" and are configured for engagement with the anchor of the anchor assembly 14, as will be further described below. The divets 11d are located at about 180° apart and are in line with grooves on the anchor assembly 14, as will be further described below. The distal portion 11b" of the inner member 11b also includes at least two prongs 11b''' configured for engagement with the insertion member of the anchor assembly 14, as will be further described below.

A suture threader 15 is also releasably coupled to the shaft 11. The threader 15 includes a clip 15a and a loop of suture 15b coupled to the clip 15a. The suture loop 15b is disposed within the transverse through hole of the anchor assembly 14 and is used during surgery to thread ends of suture from another anchor into the through hole, as further described below.

As shown more clearly in FIGS. 3-6, the means 13 includes body 13a having a distal end 13a' a proximal end 13a", wherein the distal end 13a' is housed within the opening 12e of the handle 12. The means 13 also includes an inner cavity 13b having a top portion 13b', a middle portion 13b", and a bottom portion 13b'''. The top portion 13b' and the middle portion 13b" are located in the proximal end 13a" and the bottom portion 13b''' is located between the proximal end 13a" and the distal end 13a'. The middle portion 13b" includes gears 13c. The means 13 also includes a plug 13d having a top end 13d' and a bottom end 13d". The top end 13d' is housed within the top portion 13b' of the cavity 13b and the bottom end 13d" extends between the middle portion 13b" and bottom portion 13b'''. The bottom portion 13d' includes a channel 13h for housing of the proximal portion 11b of the inner member 11 and is configured for engagement with a first portion 13e and a second portion 13f, as will be further described below.

A first portion 13e is disposed on the bottom end 13d" of the plug 13d and includes gears 13e' that are configured for engagement with the gears 13e on the middle portion 13b", as will be further described below. A second portion 13f is also disposed on the bottom end 13d" of the plug 13d and includes a groove 13f' configured for receipt of a spring 13g located between the first portion 13e and the second portion 13f. The spring 13g allows for the application of force on the first portion 13e, thereby providing engagement of the gears 13e', 13e.

Figure 8:
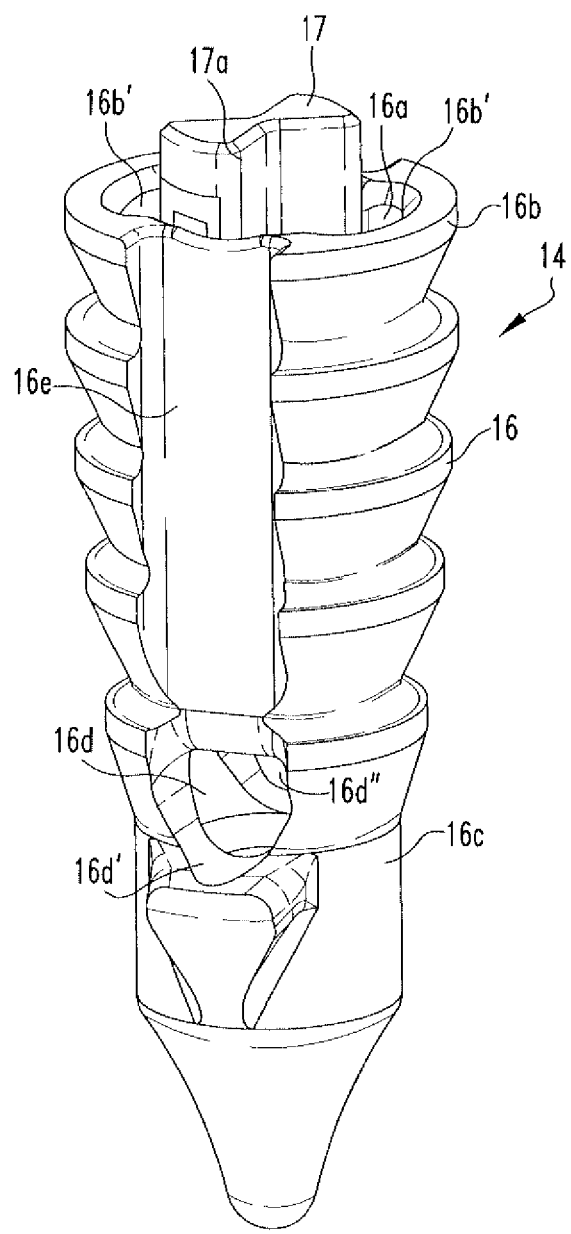
FIG. 8 shows a perspective view of the anchor assembly of the present disclosure.
Figure 9:
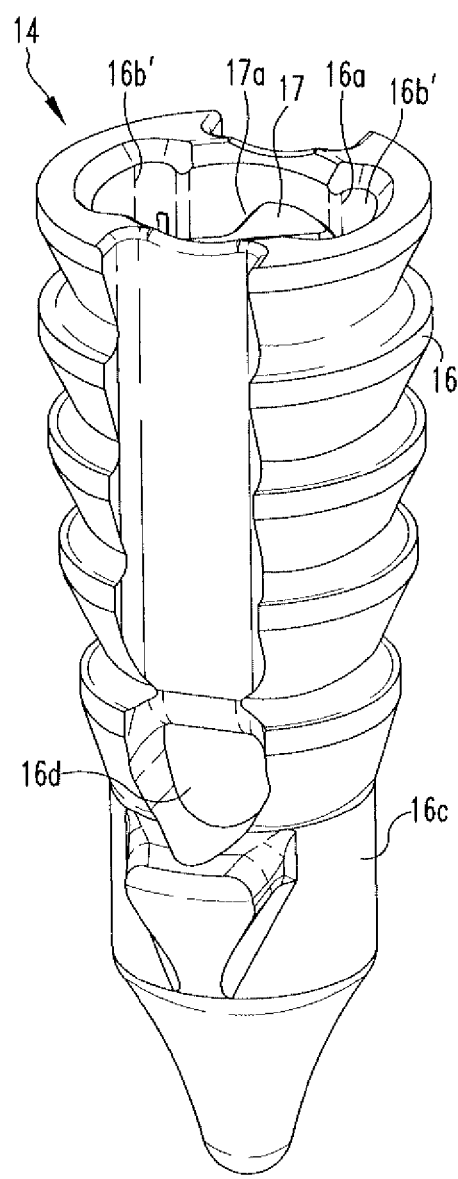
FIG. 9 shows another perspective view of the anchor assembly of the present disclosure.
Figure 10:
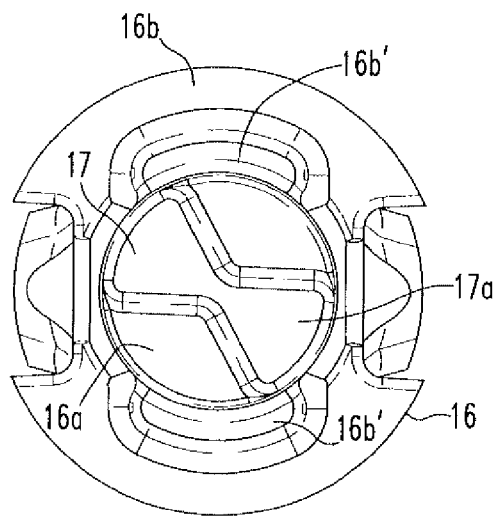
FIG. 10 shows a top view of the anchor assembly of the present disclosure.
Figure 11:
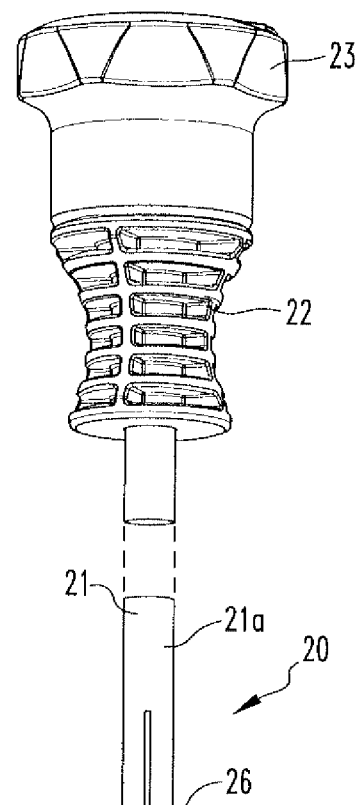
FIG. 11 shows a perspective view of a second surgical device of the present disclosure.
Figure 14:
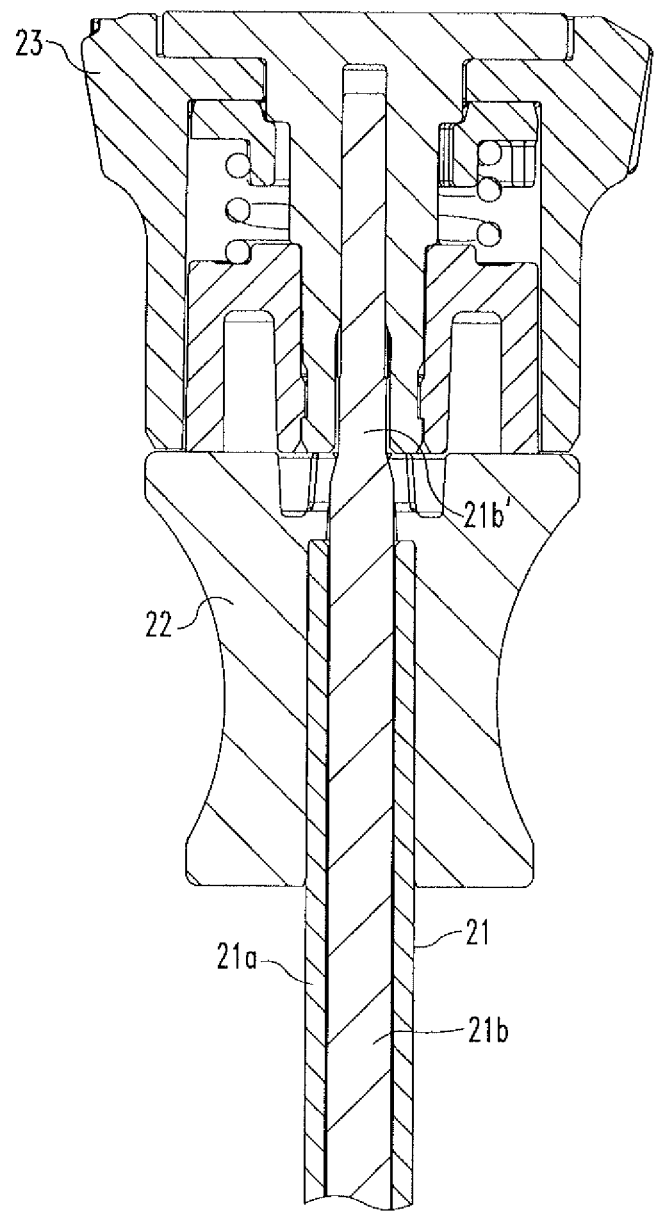
FIG. 14 shows a perspective view of the handle and means for providing movement of the inner member of the second surgical device of FIG. 11.

FIGS. 8-10 show the anchor assembly 14 of the present disclosure. The anchor assembly 14 includes an anchor 16 defining a cavity 16a and an insertion member 17 housed within the cavity 16a. The anchor 16 includes a proximal portion 16b and a distal portion 16c. The proximal portion 16b includes at least two grooves 16b' for housing of the prongs 11a''' on the outer member 11a. The insertion member 17 includes a head 17a configured for engagement with the prongs 11b''' of the inner member 11b. In addition, the anchor 16 includes a transverse through hole 16d and slots 16e extending from openings 16d',16d" of the through hole 16d to the proximal portion 16b of the anchor 16, for purposes to be described later. Other features of the anchor assembly are described and shown in U.S. Patent Application Publication No. 2009112270, the disclosure of which is incorporated herein by reference in its entirety.

FIGS. 11-14 show a second surgical device 20 of the present disclosure. Similar to the first surgical device 10, the device 20 includes a shaft 21 having an outer member 21a and an inner member 21b slidably received within the outer member 21a. A handle 22 is coupled to the shaft 21 and a means 23 for providing movement to the inner member 21b, similar to means 13 is coupled to a proximal portion 21b' of the inner member 21b. The outer member 21a is shorter than the inner member 21b, such that the distal portion 21a" of the outer member 21a ends proximal to the distal portion 21b" of the inner member 21b, as shown more clearly in FIGS. 11 and 12. The prongs 24, divets 25, and laser marks 26 of the outer member 21a are all the same as the prongs 11b, divets 11d, and laser marks 11e of the outer member 11a of the first surgical device 10. Similarly, the prongs 27 of the inner member 21b are the same as the prongs 11b''' of the inner member 11b of the device 10. In addition, the means 23 is the same as the means 13 of the device 10.

Figure 15A:
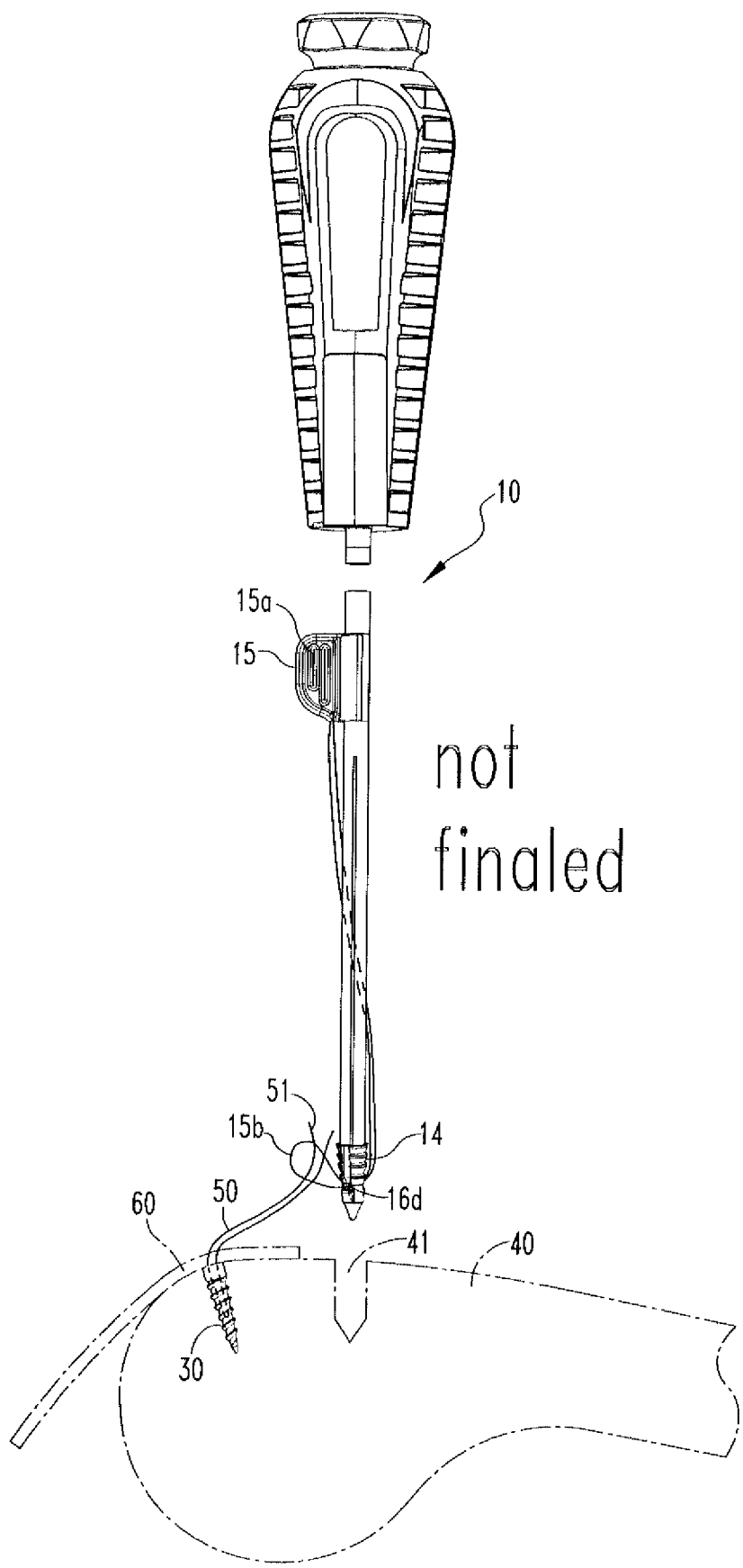

During surgery, the first surgical device 10 is used to place the anchor assembly 14 into bone. FIGS. 15A-15C show the first surgical device 10 in use during arthroscopic repair of the rotator cuff. FIG. 15A shows a first anchor 30 that has been inserted into the lateral aspect of a bone 40, such as a humeral bone. The anchor 30, which has a flexible member 50, such as a suture, coupled thereto is inserted into the bone 40, a soft tissue 60, such as a rotator cuff tendon, is placed oil the bone 40 to be located adjacent to the anchor 30, and at least one of the ends 51 of the flexible member 50 are placed through the soft tissue 60.

Next at least one end 51 of the flexible member 50 is passed through the loop 15b, as shown in FIG. 15A, and threaded through the transverse through hole 16d by pulling the loop 15b and the flexible member 50 through the transverse through hole 16d, as shown in FIG. 15B, via use of the clip 15a. After the flexible member 50 is passed through the through hole 16d, the suture threader 15 is discarded. The anchor assembly 14 is subsequently inserted into a previously drilled hole 41 in the medial aspect of the bone 40, as shown in FIG. 15C, such that the flexible member 50 is housed within the transverse through hole 16d and the ends 51 extend out of the hole 41. The anchor assembly 14 is advanced into the hole 41 in an axially-oriented manner by tapping on the means 13. As mentioned above, the first and second laser marks 11c, 11e are used for proper orientation and depth of the anchor 16 into the hole 41. Namely, the anchor 16 is placed within the hole 41 such that the first laser mark 11c is flush with the surface of the bone 40 and the second laser mark 11e allows for proper visual orientation of the anchor 16 while placing it in the bone 40.

After placement of the anchor assembly 14 into the hole 41, the ends 51 of the flexible member 50 may be pulled to provide a preferred amount of tension on the flexible member 50 and the soft tissue 60. This tension on the flexible member 50 can be seen in FIG. 15D, especially when comparing this figure to FIG. 15C. The insertion member 17 is subsequently advanced in a rotary manner, via the inner member 11b, to secure the flexible member 50 in the through hole 16d and the tissue 60 to the bone 40. For clarity purposes, the insertion member 17 is not shown in FIGS. 15C and 15D. The anchor assembly 14 is located on the distal portions 11a'',11b'' of the inner and outer members 11a,11b such that the slots 16c are in-line with the divets 11d, thereby allowing the flexible member 50 to slide and substantially reducing the member 50 from being caught between the distal portion 11a'' and the hole 41.

By rotating the means 13, the inner member 11a is rotated. Upon initial rotation of the means 13, the gears 13c,13e' are in full engagement with each other. However, once the insertion member 17 is engaged with the flexible member 50 and the flexible member 50 is secured in the through hole 16d, further rotation of the means 13 will cause downward movement of the first portion 13e toward the second portion 13f, thereby causing the gears 13c' to fall out of full engagement with the gears 13c of the inner cavity 13b. Further rotation of the means 13 will cause the gears 13c of the inner cavity 13b to slide over the gears 13e' of the first portion 13e, thereby not allowing further rotation of the insertion member 17. Not only is the means 13 used to provide movement of the inner member, but it is also used to limit the amount of torque that is applied to the insertion member 17.

After placement of the anchor assembly 14, the second surgical device 20 may be used to re-tension the flexible member 50. The device 20 is inserted into the anchor assembly 14 such that the prongs 27 on the distal portion 21b'' of the inner member 21b are engaged with the head 17a of the insertion member 17. The handle 22 is then used to slide the outer member 21a, as shown more clearly in FIGS. 13 and 14, toward the anchor assembly 14 and insert the prongs 24 into the grooves 16b' of the anchor 16. Once the inner and outer members 21b,21a are inserted into the anchor assembly 14, the means 23 is rotated to disengage the insertion member 17 from the flexible member 50. The flexible member 50 is then re-tensioned and the means 23 is subsequently rotated to advance the insertion member 17 and re-secure the flexible member 50 in the through hole 16d, as described above. The first surgical device 10 may be used to re-tension the flexible member 50, rather than the second surgical device 20.

The shafts 11,21 of the first and second surgical devices 10,20 include a stainless steel material, but may be made from any other metal or non-metal material that is bio-compatible and strong enough to withstand the forces that are placed on the shafts 11,21 during surgery. The shafts 11,21 may be machined, die drawn and subsequently machined, or made by any other method known to one of skill in the art. The shafts 11,21 are coupled to the handles 12,22 and knobs 13,23 via a press-fit procedure. However, other methods of coupling the handles 12,22 and knobs 13,23 to the shafts 11,21 are also within the scope of this disclosure. The handles 12,22 and knobs 13,23 are of a non-metal material, but may be made from a metal material, and both are made via an injection molding process. However, other methods of making are also within the scope of this disclosure.

The clip 15a is made from a non-metal material and is injection molded. However, other material, including metal materials, and processes are within the scope of this disclosure. The suture loop 15b is coupled to the clip 15a via placing a first end of the loop 15b through a hole in the clip 15a and then tying that end to a second end of the loop 15b, as shown in FIG. 2. Other methods of coupling the suture loop 15b to the clip 15a are also within the scope of this disclosure. In addition, other devices and methods of threading ends of suture from a previously placed anchor through the transverse through hole 16d are also within the scope of this disclosure.

The spring 13g is of a metal material, but may be of a non-metal material. In addition, other means of providing force resistance, other than the spring 13g, may also be used. The divets 11d are made via a machining process or other process known to one of skill in the art for making markings, such as the divets 11d, on the shafts 11,21.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical system comprising:
   a shaft including an outer member and an inner member slidably received within the outer member, the outer member including prongs extending from a distal portion of the outer member and the inner member including prongs extending from a distal portion of the inner member, the inner member including a solid core extending from the distal end of the inner member to a proximal end of the inner member;

a handle coupled to the outer member;

a means for providing movement to the inner member coupled to the inner member and housed within an opening in the handle, the means including a body having a distal end, a proximal end, and an inner cavity, the inner cavity including a top portion, a middle portion having gears, and a bottom portion, a plug including a top end housed within the top portion of the inner cavity and a bottom end coupled to the top end, the bottom end extending between the middle and bottom portions of the inner cavity, a first portion housed within the bottom portion of the inner cavity and disposed on the bottom end of the plug, the first portion having gears in engagement with gears of the inner cavity middle portion, a second portion housed within the inner cavity bottom and disposed on the bottom end of the plug, and a spring located between the first and second portions, the spring received within a groove of the second portion, wherein the proximal end of the inner member is housed within a channel of the plug;

an anchor assembly coupled to the shaft, the anchor assembly comprising an anchor defining a cavity, a transverse through hole extending through the anchor, and an insertion member housed within the cavity, the outer member prongs disposed within grooves of the anchor and the inner member prongs in engagement with the inner member; and a suture threader releasably coupled to the outer member, the threader comprising a clip and a suture coupled to the clip to form a loop, a portion of the loop housed within the through hole of the anchor.

2. The surgical system of claim 1 wherein the outer member is shorter than the inner member.

* * * * *